United States Patent
Ishida

(10) Patent No.: US 10,569,056 B2
(45) Date of Patent: Feb. 25, 2020

(54) CATHETER ASSEMBLY

(71) Applicant: TERUMO KABUSHIKI KAISHA, Tokyo (JP)

(72) Inventor: Masahiro Ishida, Hadano (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 491 days.

(21) Appl. No.: 15/295,580

(22) Filed: Oct. 17, 2016

(65) Prior Publication Data
US 2017/0028172 A1 Feb. 2, 2017

Related U.S. Application Data

(63) Continuation of application No. PCT/JP2016/063602, filed on May 2, 2016.

(30) Foreign Application Priority Data

May 15, 2015 (JP) .................................. 2015-100360

(51) Int. Cl.
*A61M 25/06* (2006.01)
*A61M 25/01* (2006.01)

(52) U.S. Cl.
CPC .... *A61M 25/0606* (2013.01); *A61M 25/0612* (2013.01); *A61M 25/0618* (2013.01); *A61M 25/0113* (2013.01)

(58) Field of Classification Search
CPC .................... A61M 25/0606; A61M 25/0612
See application file for complete search history.

(56) References Cited

U.S. PATENT DOCUMENTS

2009/0131870 A1* 5/2009 Fiser ................. A61M 25/0618
604/162
2016/0220270 A1* 8/2016 Tamura ............. A61M 25/0631

FOREIGN PATENT DOCUMENTS

| JP | 2013-529111 A | 7/2013 |
|---|---|---|
| JP | 2015-051259 A | 3/2015 |
| WO | WO-2011/143621 A1 | 11/2011 |
| WO | WO-2014/133617 A1 | 9/2014 |
| WO | WO-2014/196051 A1 | 12/2014 |
| WO | WO-2014/196243 A1 | 12/2014 |

OTHER PUBLICATIONS

International Searching Authority, "International Search Report," issued in connection with International Patent Application No. PCT/JP2016/063602, dated Jul. 26, 2016.
International Searching Authority, "Written Opinion," issued in connection with International Patent Application No. PCT/JP2016/063602, dated Jul. 26, 2016.

* cited by examiner

*Primary Examiner* — Nathan R Price
*Assistant Examiner* — Tasnim Mehjabin Ahmed
(74) *Attorney, Agent, or Firm* — Foley & Lardner LLP

(57) ABSTRACT

A catheter assembly including a catheter; a catheter hub fixed to a proximal end portion of the catheter; an inner needle disposed inside the catheter; and a housing supporting the inner needle, the housing accommodating the catheter hub when in an initial state in which a distal end of the inner needle is protruding from a distal end of the catheter. The catheter hub is configured to rotate with respect to the inner needle and the housing when accommodated inside the housing.

20 Claims, 13 Drawing Sheets

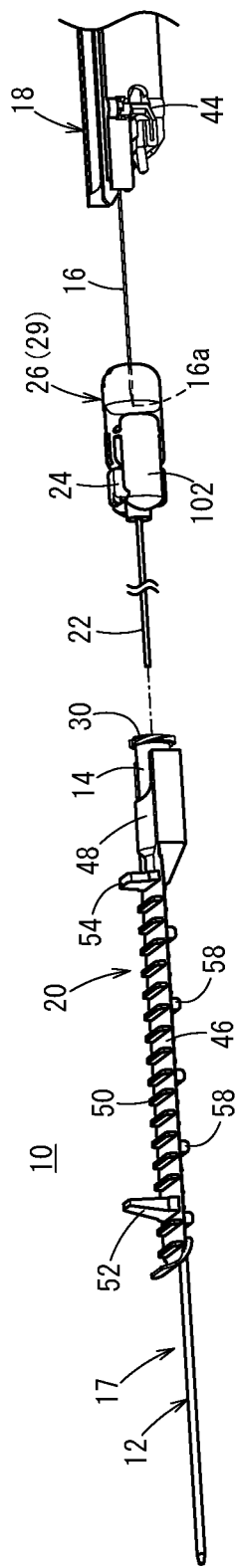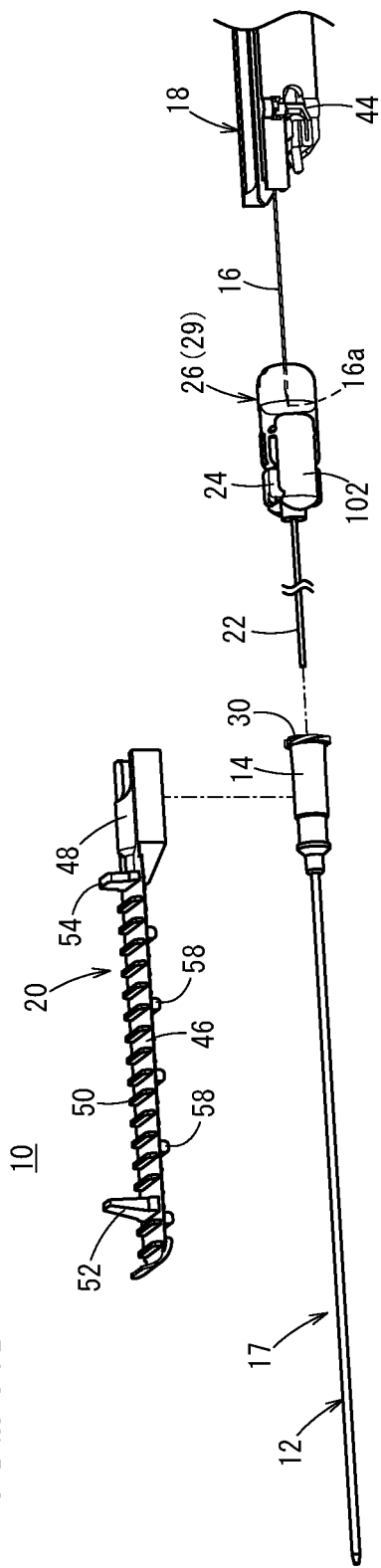

CATHETER ASSEMBLY

CROSS-REFERENCE TO RELATED APPLICATIONS

This application is a continuation of PCT Application No. PCT/JP2016/063602, filed on May 2, 2016, which claims priority to Japanese Application No. 2015-100360, filed on May 15, 2015. The contents of both of these applications are hereby incorporated by reference in their entireties.

BACKGROUND

The present disclosure relates to a catheter assembly which is to pierce and to remain in a blood vessel of a patient at a time of transfusion, for example.

Conventionally, at the time of performing transfusion in a patient, a catheter assembly is used, for example. This type of catheter assembly includes a hollow catheter, a catheter hub secured to a proximal end of the catheter, a hollow inner needle inserted inside the catheter and having a sharp needle tip at a distal end, and a needle hub secured to a proximal end of the inner needle. To reduce the puncture resistance, the diameter of the catheter distal end is reduced, and a catheter inner surface and an inner needle outer surface are in close contact with each other at the reduced diameter part. When this close contact continues for a long time, the catheter inner surface and the inner needle outer surface become adhered to each other, and it becomes difficult to perform operation of moving the catheter forward with respect to the inner needle in order to insert the catheter into a blood vessel. Accordingly, with a conventional catheter assembly having a structure where a catheter hub is connected to a distal end of a needle hub, in many cases, adhesion is released by relatively rotating the catheter hub and the needle hub before piercing.

SUMMARY

With the catheter assembly disclosed in JP 2013-529111 A, in an initial state, a catheter hub is accommodated inside a housing (needle hub), and a catheter operation section is connected to the catheter hub. Although the catheter operation section and the housing are allowed to slide in a front-back direction, they are not allowed to relatively rotate with respect to each other, and adhesion of a catheter inner surface and an inner needle outer surface cannot be released by the method described above. Accordingly, the catheter assembly of JP 2013-529111 A adopts, as an alternative method, a method of releasing adhesion of the catheter inner surface and the inner needle outer surface by moving the catheter forward and backward several millimeters with respect to the inner needle. However, with this alternative method, there is a risk of piercing the catheter with an inner needle distal end at the time of moving the catheter backward.

Embodiments of the present invention have been made in view of such a problem, and have an aim to provide a catheter assembly, including a catheter hub accommodated in a housing, that is configured to release adhesion of a catheter inner surface and an inner needle outer surface by relative rotation of an inner needle and a catheter.

To achieve the above object, a catheter assembly includes: a catheter; a catheter hub fixed to a proximal end portion of the catheter; an inner needle inserted through the catheter; and a housing for supporting the inner needle, and for accommodating the catheter hub in an initial state where a distal end of the inner needle is protruding from a distal end of the catheter, wherein the catheter hub is configured to rotate with respect to the inner needle and the housing while being accommodated inside the housing.

According to the catheter assembly of the embodiment configured in the above manner, the catheter hub accommodated inside the housing can be rotated with respect to the inner needle and the housing. Accordingly, adhesion of the catheter inner surface and the inner needle outer surface may be released by rotating the catheter hub supporting the catheter before using the catheter assembly.

In the catheter assembly, the catheter hub may be, in the initial state, configured to rotate with respect to the inner needle and the housing.

According to this structure, adhesion of the catheter inner surface and the inner needle outer surface may be released even more easily before using the catheter assembly.

In the catheter assembly, the catheter hub may be configured to rotate with respect to the inner needle and the housing over an entire range from a first position corresponding to the initial state to a second position after forward movement by a predetermined distance with respect to the housing.

According to this structure, when the distal end of the catheter gets caught on a blood vessel wall during insertion of the catheter into a blood vessel, a procedure of inserting the catheter into the blood vessel while rotating the same may be taken.

The catheter assembly may further include a rotation operation section coupled to the catheter hub in a manner not configured for relative rotation, and the rotation operation section may be exposed from the housing in a state where the catheter hub is accommodated inside the housing.

According to this structure, because the rotation operation section exposed from the housing may be touched and rotated by hand, adhesion may be easily released.

In the catheter assembly, the rotation operation section may be capable of being detached from the catheter hub.

According to this structure, the part that is made to remain on the skin of a patient may be made small.

The catheter assembly may further include: an auxiliary member disposed between the catheter and the inner needle, along the catheter; and an auxiliary member hub fixed to a proximal end portion of the auxiliary member, and the catheter hub and the rotation operation section may be coupled through the auxiliary member hub in a manner not capable of relative rotation.

According to this structure, rotation of the rotation operation section is transmitted to the catheter through the auxiliary member hub and the catheter hub, and the catheter may be rotated.

The catheter assembly may further include a catheter operation member connected to the catheter hub and configured to be displaced with respect to the housing, along a longitudinal direction of the housing, and the catheter hub is configured to rotate with respect to the catheter operation member and the catheter.

According to this structure, even in a case where a catheter operation section is provided, rotation of the catheter hub is not obstructed by the catheter operation section, and thus, adhesion of the catheter and the inner needle may be reliably released.

In the catheter assembly, the rotation operation section may form a needle protection member for covering at least a distal end of the inner needle when the inner needle is removed from the catheter.

According to this structure, because the rotation operation section functions also as the needle protection member, the rotation operation section and the needle protection member do not have to be separately provided, and an increase in the number of components or complication of the structure caused by having to provide the rotation operation section may be suppressed.

In the catheter assembly, the housing may be provided with an opening portion for exposing the rotation operation section.

According to this structure, the rotation operation section may be easily rotated, and the operability is enhanced.

According to this catheter assembly of certain embodiments of the present invention, adhesion of the catheter inner surface and the inner needle outer surface may be released by relative rotation of the inner needle and the catheter.

BRIEF DESCRIPTION OF THE DRAWINGS

FIG. 13A is a third view describing the method of using the catheter assembly, and FIG. 13B is a fourth view describing the method of using the catheter assembly.

DETAILED DESCRIPTION

Hereinafter, embodiments of a catheter assembly according to the present invention will be described with reference to the appended drawings.

Figure 1:
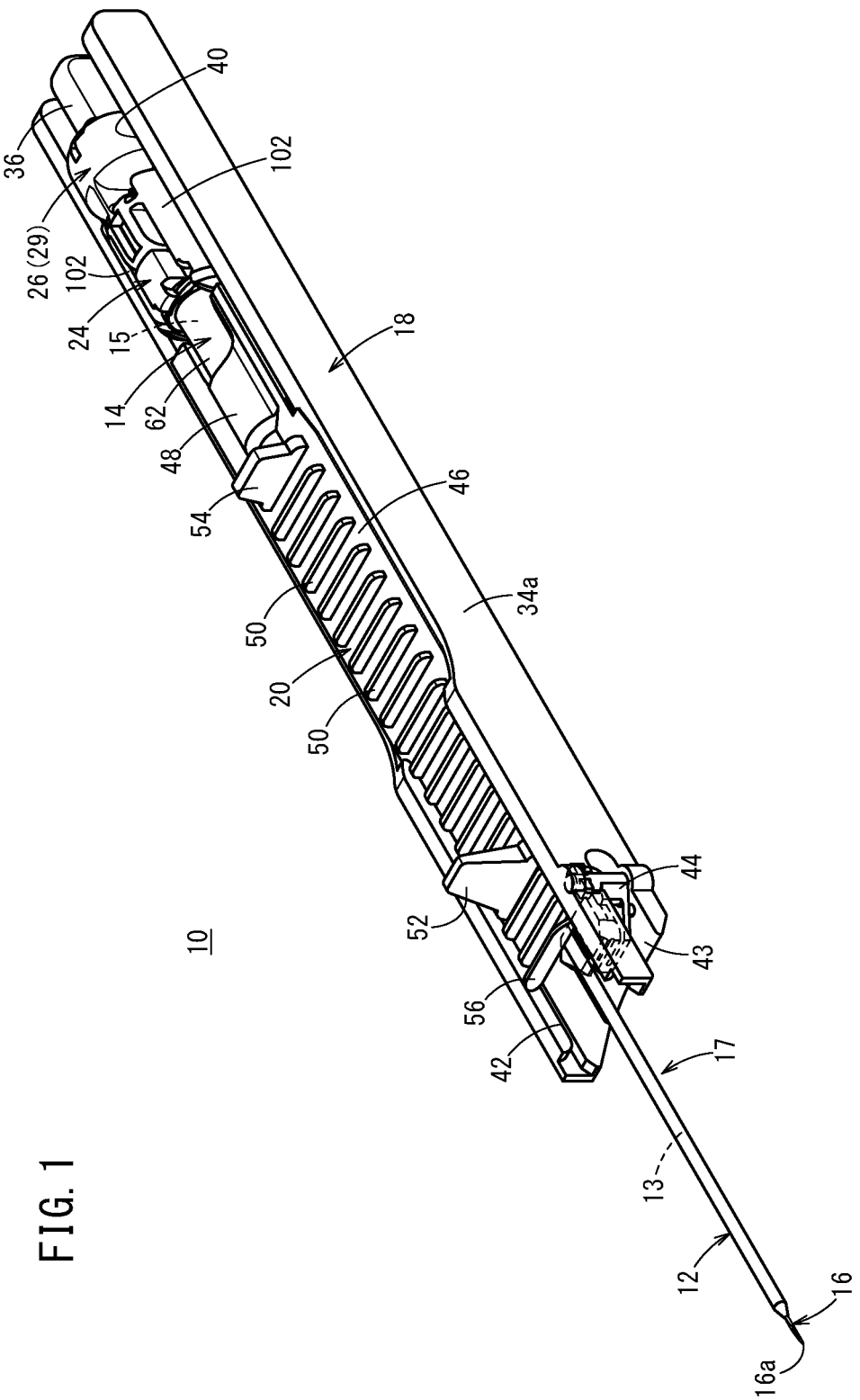
FIG. 1 is a perspective view of a catheter assembly according to an embodiment of the present invention.

A catheter assembly 10, whose initial state is illustrated in FIG. 1, is used in performing a transfusion, a blood transfusion or the like in a patient (a living body), and configures an introduction section for a drug solution or the like, which pierces and is caused to remain inside the body of the patient. The catheter assembly 10 may be configured as a catheter that is longer than a peripheral venous catheter (such as a central venous catheter, a PICC, or a mid-line catheter). The catheter assembly 10 may alternatively be configured as the peripheral venous catheter. The catheter assembly 10 is not limited to a venous catheter, and may alternatively be configured as an arterial catheter, such as a peripheral arterial catheter.

Figure 2:
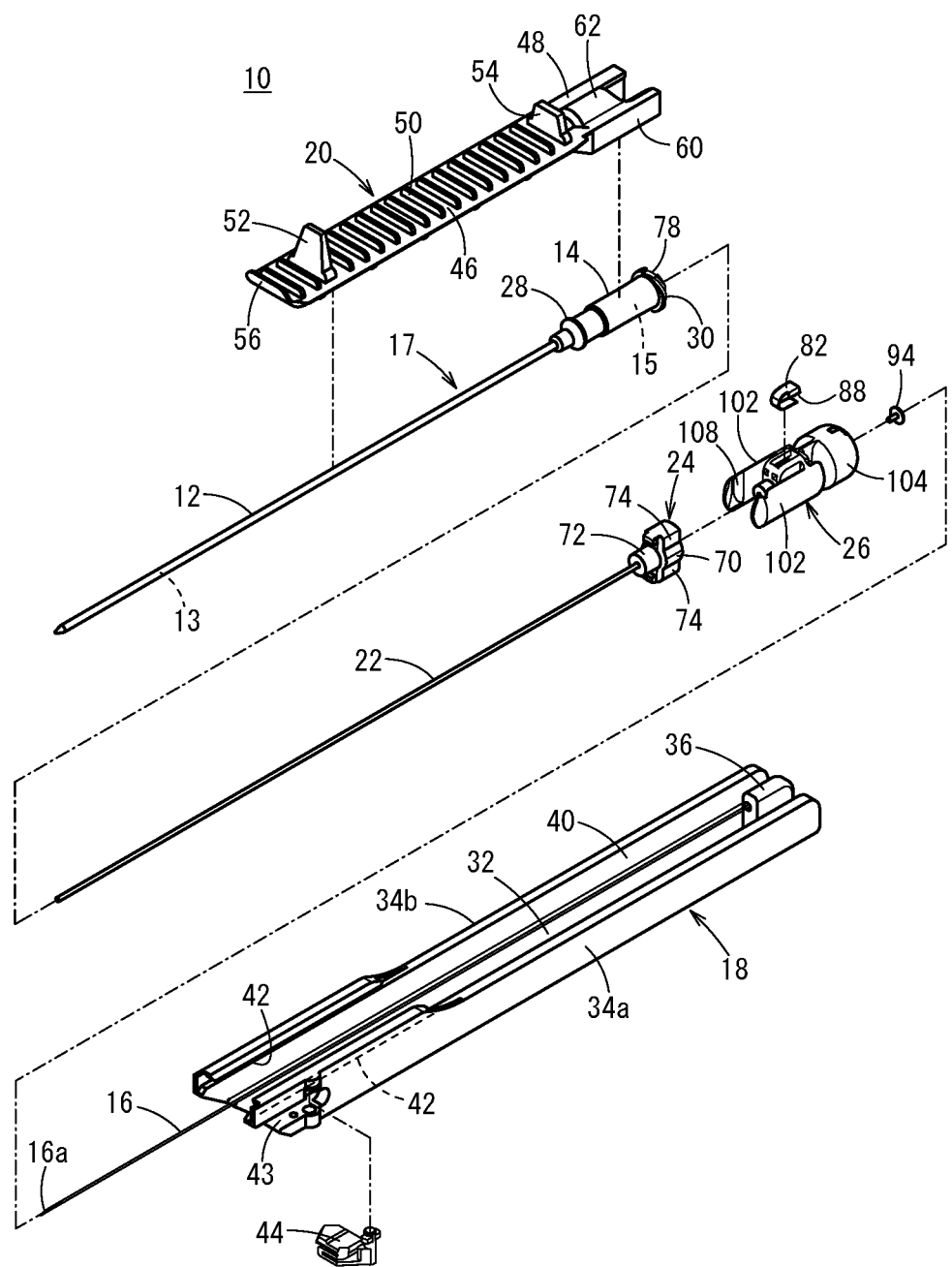
FIG. 2 is an exploded perspective view of the catheter assembly illustrated in FIG. 1.

As illustrated in FIGS. 1 and 2, the catheter assembly 10 includes a catheter 12, a catheter hub 14 for fixedly holding the catheter 12, a hollow inner needle 16 to be inserted into catheter 12 in a manner capable of being removed, a housing 18 for fixedly holding the inner needle 16, a catheter operation member 20 to be attached to an upper side of the catheter hub 14, an auxiliary member 22 to be inserted between the catheter 12 and the inner needle 16 in a manner capable of being removed, an auxiliary member hub 24 for fixedly holding the auxiliary member 22, and a needle protection member 26 to be connected to proximal ends of the catheter hub 14 and the auxiliary member hub 24. Additionally, the inner needle 16 may be partially cut out along an axial direction. Also, the inner needle 16 may be a solid needle.

In the initial state before use, the catheter assembly 10 forms a multi-tube structure (a multi-tube section) where the catheter 12, the auxiliary member 22, and inner needle 16 are overlapped with one another in this order. The catheter operation member 20 is configured to directly hold the multi-tube section. Moreover, with the catheter assembly 10, in the initial state, a part of the multi-tube section, the catheter hub 14, the auxiliary member hub 24, the needle protection member 26, and the catheter operation member 20 are accommodated inside the housing 18.

The catheter 12 is flexible, and has a lumen 13 formed penetrating through the inside. The lumen 13 is formed with a diameter allowing accommodation of the inner needle 16 and the auxiliary member 22 and flowing of a drug solution, blood or the like. To reduce the puncture resistance, the diameter of the distal end of the catheter 12 is reduced, and in the initial state of the catheter assembly 10, the inner surface of the catheter 12 and the outer surface of the inner needle 16 are in close contact with each other at the reduced diameter part. The length of the catheter 12 may be designed as appropriate according to use or various conditions without being particularly limited, and is set to about 14 mm to 500 mm, or to about 30 mm to 400 mm, or to about 76 mm to 200 mm, for example.

The constituent material of the catheter 12 is not particularly limited, but a soft resin material is suitably used. For example, a fluorine-based resin such as polytetrafluoroethylene (PTFE), ethylene-tetrafluoroethylene copolymer (ETFE) or perfluoroalkoxy fluorine resin (PFA), an olefin-based resin such as polyethylene or polypropylene or a mixture thereof, polyurethane, polyester, polyamide, polyether nylon resin, or a mixture of the olefin-based resin and ethylene-vinyl acetate copolymer may be cited.

A proximal end portion of the catheter 12 is secured to a distal end portion inside the catheter hub 14 by an appropriate securing method (crimping, fusion, adhesion, etc.). The catheter 12 and the catheter hub 14 form a catheter member 17.

The catheter hub 14 is exposed on the skin of a patient with the catheter 12 inserted in a blood vessel, and is caused to remain on the skin by being attached by a tape or the like, together with the catheter 12. The catheter hub 14 is formed to have a cylindrical shape which is tapered toward the distal end.

The constituent material of the catheter hub 14 is not particularly limited, but a thermoplastic resin material, such as polypropylene, polycarbonate, polyamide, polysulfone, polyarylate or methacrylate-butylene-styrene copolymer, may be suitably used.

A hollow section 15 which communicates with the lumen 13 of the catheter 12 and through which a transfusion is allowed to flow is provided inside the catheter hub 14. A hemostatic valve, a plug or the like, not shown, is accommodated inside the hollow section 15 in order to prevent back-flow of blood at the time of piercing by the inner needle 16, and to allow transfusion by insertion of a connector of a transfusion tube.

As illustrated in FIG. 2, a circular protrusion 28 protruding radially outward and extending in the circumferential direction of the catheter hub 14 is formed on the outer circumferential surface, near the distal end, of the catheter hub 14. A screw section 30 protruding radially outward in a flange shape and extending in the circumferential direction is provided at a proximal end side of the catheter hub 14, and a connector of a transfusion tube, not shown, is connected thereto after the inner needle 16 is detached.

The inner needle 16 of the catheter assembly 10 is configured as a hollow tube with a rigidity allowing the inner needle 16 to pierce through the skin of a living body, and is disposed inside the lumen 13 of the catheter 12 and the hollow section 15 of the catheter hub 14. The inner needle 16 has a total length longer than the catheter 12, and a sharp needle tip 16a is provided at its distal end.

In the initial state illustrated in FIG. 1, the multi-tube section has the needle tip 16a exposed from the catheter 12 and the auxiliary member 22. A lumen penetrating the inner needle 16 in the axial direction is provided inside the inner needle 16, and the lumen is communicated with a distal end opening of the inner needle 16. Additionally, a groove section for checking flashback may be provided on the outer circumferential surface of the inner needle 16, along the axial direction.

As the constituent material of the inner needle 16, a metal material, such as stainless steel, aluminum or aluminum alloy, or titanium or titanium alloy, a hard resin, or ceramics may be cited. The inner needle 16 is firmly secured to the housing 18 by an appropriate securing method (fusion, adhesion, insert molding, etc.).

As illustrated in FIG. 2, the housing 18 includes a lower wall 32, a pair of side walls 34a, 34b protruding upward from sides of the lower wall 32, and a needle holding section 36, protruding upward from an upper surface of the lower wall 32, for fixedly supporting a proximal end portion of the inner needle 16. Moreover, the upper part of the housing 18 is open.

An accommodation space 40 for accommodating a part of the multi-tube section, the catheter hub 14, the auxiliary member hub 24, and the needle protection member 26 is formed on the inside surrounded by the lower wall 32 and the pair of side walls 34a, 34b. The resin material forming the housing 18 is not particularly limited, and may be selected as appropriate from the materials cited for the catheter hub 14, for example.

The pair of side walls 34a, 34b is formed in parallel in a longitudinal direction together with the lower wall 32, and the vertical widths on the proximal end side and at the mid-portion are fixed, and the vertical width on the distal end side is wider than the vertical width at the mid-portion. A groove-shaped rail section 42 is provided on an upper part of each side wall 34a, 34b, on the distal end side, the rail section 42 being formed by linearly cutting out the inner surface of the side wall 34a, 34b. The rail sections 42 accommodate left and right side edges of the catheter operation member 20, and guide forward and backward movement of the catheter operation member 20. A concave section 43 for arrangement, which is for mounting a support member 44, is provided to one side wall 34a.

The housing 18 holds the inner needle 16 at the needle holding section 36, and when the housing 18 is moved in the direction of the proximal end with respect to the catheter 12, the inner needle 16 is also moved, according to the movement of the housing 18, in the direction of the proximal end with respect to the catheter 12. That is, the housing 18 functions also as a needle hub fixed to the proximal end of the inner needle 16. Additionally, the lower wall 32 and the side walls 34a, 34b are illustrated to have flat surfaces, but may instead have curved surfaces.

According to the catheter assembly 10, in order to allow relative rotation of the catheter 12 with respect to the inner needle 16, upper parts of the catheter hub 14 and the needle protection member 26 are exposed from the housing 18. The catheter assembly 10 may be formed to cover the catheter hub 14, the needle protection member 26, and the like by forming an upper wall to the housing 18 or by mounting a lid.

The catheter operation member 20 causes the catheter 12 and the catheter hub 14 to move forward or backward with respect to the inner needle 16 and the housing 18, by directly holding the catheter 12 and by being attached to the catheter hub 14. Specifically, the catheter operation member 20 includes an operation plate section 46 extending in the distal end/proximal end direction, and a hub attachment section 48 which is integrally molded with the proximal end of the operation plate section 46 and which is attached to the catheter hub 14 in a freely detachable manner.

The operation plate section 46 is a part where the finger of a user touches to perform an operation of moving the catheter 12 forward or backward. Left and right side edges extending along the longitudinal direction of the operation plate section 46 are disposed on the upper surfaces of the pair of side walls 34a, 34b and in the pair of rail sections 42.

By being formed sufficiently thinly, the operation plate section 46 is made flexible so as to be able to easily bend in a direction orthogonal to the plane direction of the operation plate section 46 in a side view. The constituent material of the operation plate section 46 (the catheter operation member 20) is not particularly limited, and may be selected as appropriate from the materials cited for the catheter hub 14, for example.

Ribs 50 and tabs 52, 54 are provided on the upper surface of the operation plate section 46, and a distal end curved section 56 is provided at the distal end of the operation plate section 46.

A plurality of ribs 50 are provided along the longitudinal direction of the operation plate section 46 at regular intervals at other than where the tab 52 is formed. The strength of the operation plate section 46 in the width direction is increased by the plurality of ribs 50 slightly protruding upward and also extending straight along the width direction of the operation plate section 46. Accordingly, the operation plate section 46 is prevented from being bent, for example, inside the housing 18 even when a pressure is applied from outside, and may smoothly move forward or backward in the direction of the distal end or the proximal end along the side walls 34a, 34b and the rail sections 42. The tab 52 is a part assumed to be directly touched by the finger of a user, and is formed protruding higher than the ribs 50. Additionally, the ribs 50 do not have to be disposed at regular intervals.

Figure 3:
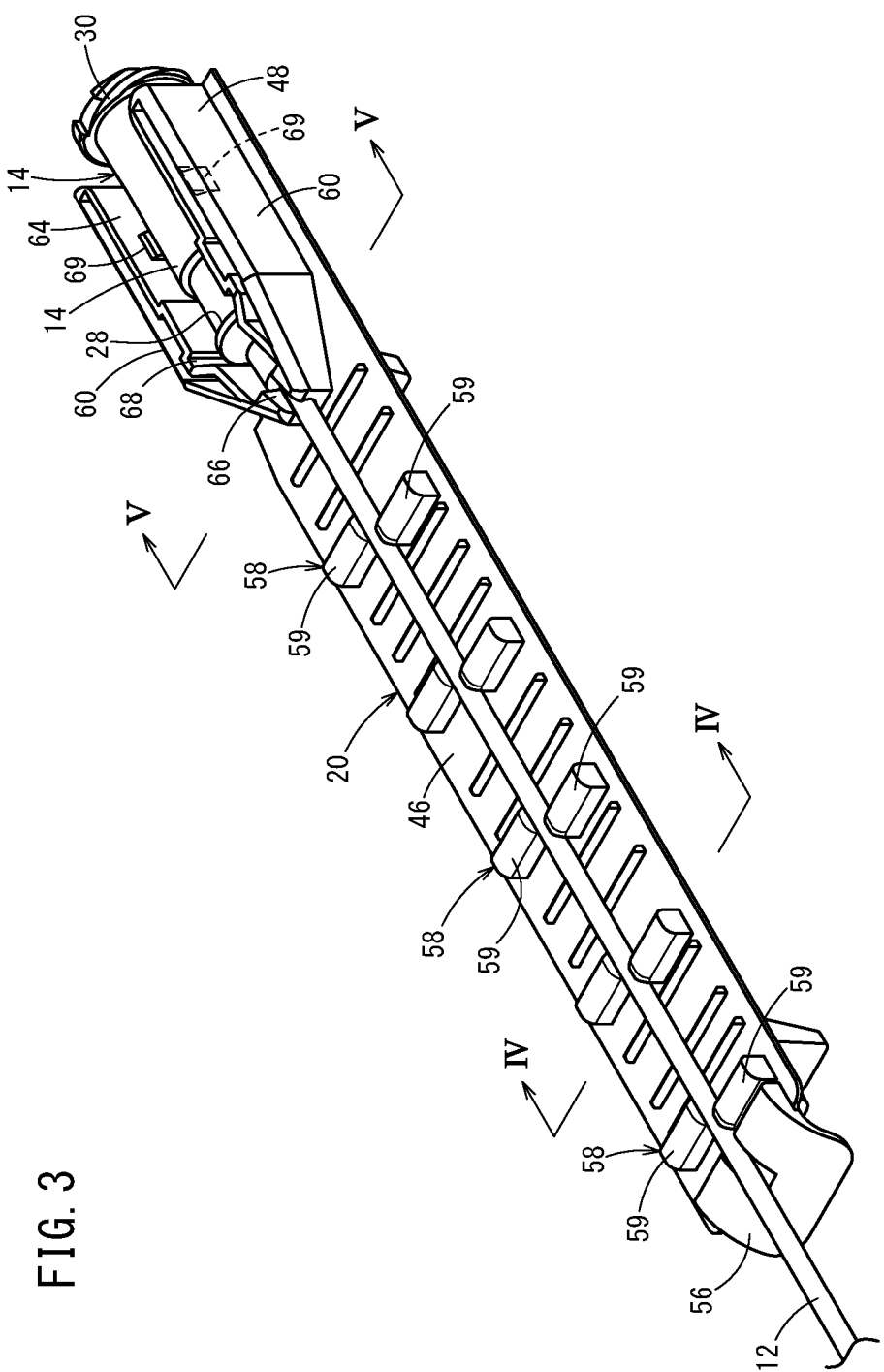
FIG. 3 is a perspective view of a catheter operation member attached to a catheter member, seen from below.

As illustrated FIG. 3, a plurality (in the drawing, five) of holding section 58 for holding the multi-tube section, including the catheter 12, in a freely detachable manner are formed at intervals on the lower surface of the operation plate section 46, in the longitudinal direction of the operation plate section 46. Additionally, only the structural elements necessary for description are illustrated in FIG. 3. Each holding section 58 includes a pair of left and right protruding pieces 59. Each protruding piece 59 protrudes downward from the lower surface of the operation plate section 46. Additionally, it is also possible to provide only one holding section 58, or to not provide the holding section 58.

The hub attachment section 48 is formed to have a box shape by a pair of side plates 60 protruding downward from the operation plate section 46, and semi-cylindrical upper plate 62 (see FIG. 2) slightly protruding upward from the operation plate section 46. When seen from below, the pair of side plates 60 extends in parallel on the proximal end side and at mid-portion, and the distal end side continuous to the mid-portion is inclined inward toward the distal end.

An attachment chamber 64 is provided inside the hub attachment section 48, for rotatably accommodating the catheter hub 14 and for restricting movement of the catheter hub 14 in the axial direction with respect to the hub attachment section 48. The attachment chamber 64 is open to the outside at a lower part and a proximal end of the hub attachment section 48.

At the attachment chamber 64, a fitting groove 66 formed by continuous trapezoid and circular holes, a groove section 68 where the pair of side plates 60 and the upper plate 62 are extended in a U shape, and a pair of protrusions 69 protruding on the inside of the hub attachment section 48 are formed. The catheter 12 is caught at a boundary portion of the trapezoid hole and the circular hole, and is fitted in the fitting groove 66 with an appropriate holding force. The groove section 68 rotatably accommodates the circular protrusion 28 of the catheter hub 14 while restricting movement in the direction of the distal end and the proximal end. Also, the outer circumferential surface of the catheter hub 14 is caught by the pair of protrusions 69 with a small engaging force.

The hub attachment section 48 thereby maintains the fitted state of the catheter 12 and the catheter hub 14 when in the accommodation space 40 of the housing 18. On the other hand, when the catheter operation member 20 is pulled upward out of the housing 18 by a user, the catheter hub 14 is removed from the attachment chamber 64, and the catheter 12 and the catheter hub 14 are allowed to be easily detached from each other.

Additionally, the hub attachment section 48 may be any shape and is not limited to the shape illustrated in the drawing as long as attachment/detachment of the catheter hub 14, forward movement of the catheter hub 14 by operation in the distal end direction, and rotation of the catheter hub 14 are allowed.

Figure 4:
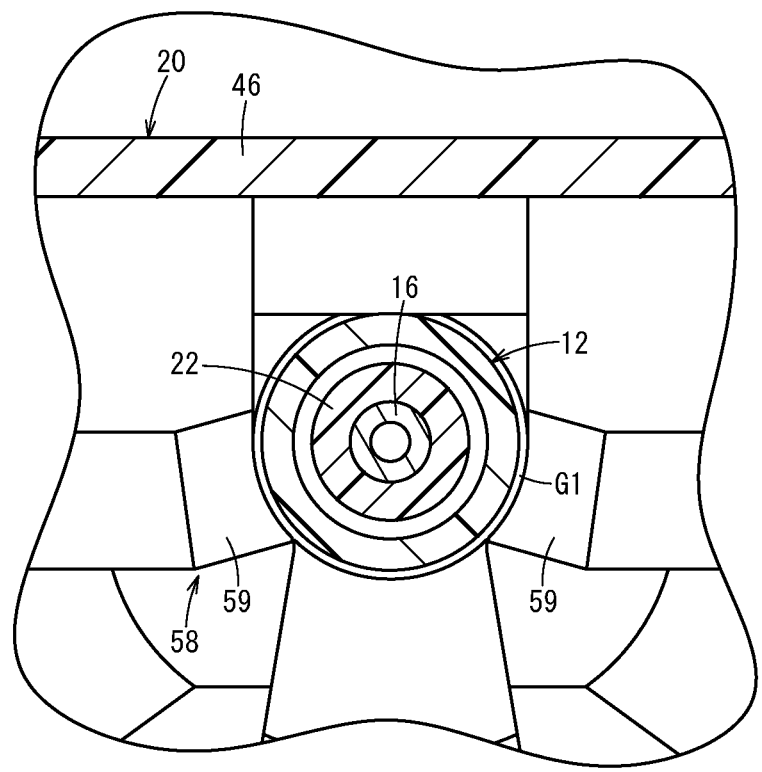
FIG. 4 is a cross-sectional view along a line IV-IV in FIG. 3.
Figure 5:
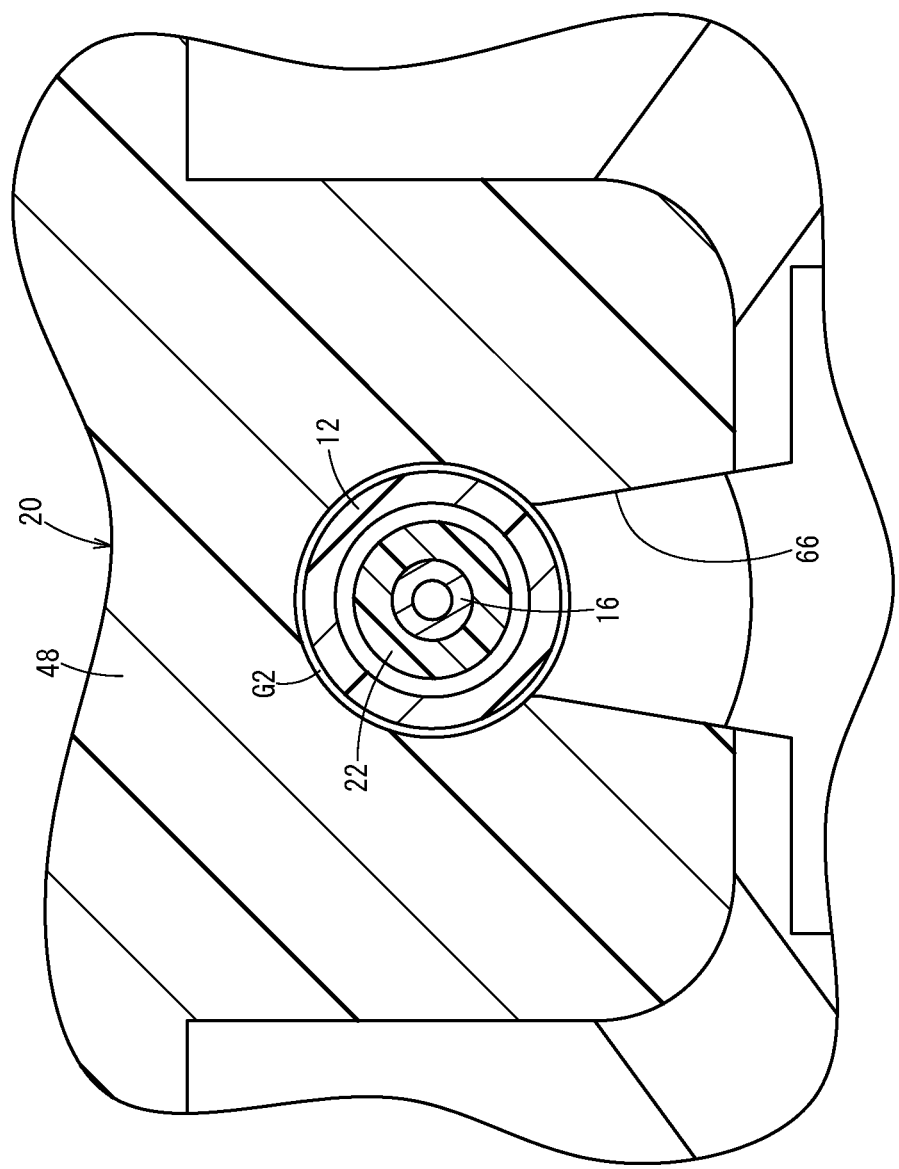
FIG. 5 is a cross-sectional view along a line V-V in FIG. 3.

The catheter 12 and the catheter hub 14 are capable of rotating with respect to the housing 18, the inner needle 16, and the catheter operation member 20. In order not to interrupt relative rotation of the catheter 12 with respect to the catheter operation member 20, appropriately small gaps G1 (see FIG. 4) and G2 (see FIG. 5) are provided between the protruding pieces 59 forming the holding section 58 and the catheter 12, and between the fitting groove 66 (circular hole) and the catheter 12, respectively. However, the outer surface of the catheter 12 may be partially in contact with the inner edges of the protruding pieces 59. Additionally, FIG. 4 is a cross-sectional view along a line IV-IV in FIG. 3, and FIG. 5 is a cross-sectional view along a line V-V in FIG. 3.

Figure 6:
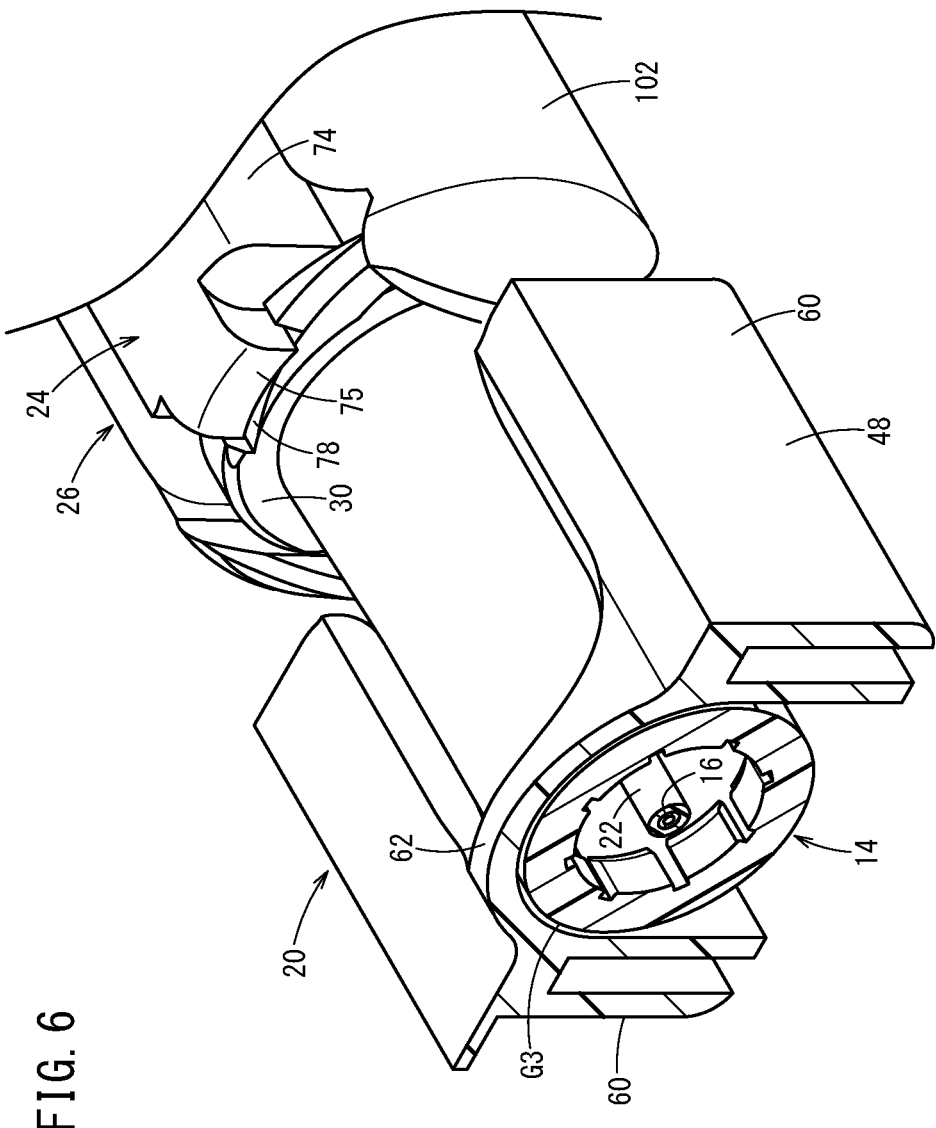
FIG. 6 is a perspective cross-sectional view of a catheter hub and a hub attachment section.

Also, in order not to interrupt relative rotation of the catheter hub 14 with respect to the catheter operation member 20, an appropriately small gap G3 (see FIG. 6) is provided between the hub attachment section 48 and the catheter hub 14. However, the outer surface of the catheter hub 14 may be partially in contact with the inner surface of the hub attachment section 48.

Additionally, the catheter operation member 20 does not necessarily have to be provided to the catheter assembly 10.

As illustrated in FIGS. 1 and 2, the catheter assembly 10 has the support member 44 provided on the distal end side of the housing 18 so as to support the lower side of the catheter 12 held by the catheter operation member 20. The support member 44 is rotatably mounted on the concave section 43 for arrangement.

The support member 44 is positioned at a region, in the housing 18, including directly under the catheter 12, in a state where the catheter operation member 20 is accommodated inside the housing 18. Accordingly, when downward pressure is applied to the catheter operation member 20 according to an operation by a user, the support member 44 supports the catheter 12 from below and warping of the catheter 12 and the inner needle 16 is suppressed. On the other hand, at the time of coming out from the housing 18, the catheter operation member 20 is rotated toward outside the side wall 34a by being pushed by the hub attachment section 48. The support member 44 may thereby cause the catheter hub 14 and the needle protection member 26 to be smoothly detached from the housing 18. Additionally, the support member 44 does not necessarily have to be provided.

Referring to FIG. 2, the auxiliary member 22 is a long flexible member inserted inside the catheter 12 in a freely detachable manner in order to prevent damage to the inner surface of the catheter 12 by the distal end of the inner needle 16 and to increase the rigidity of the catheter 12 at the time of insertion of the catheter 12 into a blood vessel. Specifically, in the initial state of the catheter assembly 10, the auxiliary member 22 is disposed between the catheter 12 and the inner needle 16, in the extending direction of the catheter 12. In the present embodiment, the auxiliary member 22 is formed as a tube, and the inner needle 16 is inserted through the lumen of the auxiliary member 22.

In the case of the present embodiment, in the initial state of the catheter assembly 10, a most distal end portion of the auxiliary member 22 is positioned nearer to the proximal end than a most distal end portion of the catheter 12 is. The most distal end portion of the auxiliary member 22 may be at the same position as the most distal end portion of the catheter 12 or may be positioned more on the distal end side than the most distal end portion of the catheter 12. In this case, the diameter of the distal end of the auxiliary member 22 is reduced so as to reduce the resistance at the time of piercing. The inner surface of the auxiliary member 22 and the outer surface of the inner needle 16 are in close contact with each other at the reduced diameter part. When the close contact continues for a long time, the inner surface of the auxiliary member 22 and the outer surface of the inner needle 16 become adhered to each other, and it becomes difficult to perform operation of moving the auxiliary member 22 forward with respect to the inner needle 16 in order to insert the auxiliary member 22 into the blood vessel, but adhesion is released by rotating the auxiliary member 22 with respect to the inner needle 16.

The auxiliary member 22 is not limited to having a tubular shape, and may alternatively have a shape whose cross-section is a C shape with a part of a circular shape cut out in the circumferential direction, or a shape with an arc-shaped cross-section which is less than 180 degrees in the circumferential direction. Also, the auxiliary member 22 may be formed as a coil or a mesh, for example, with a gap penetrating the auxiliary member 22 from the inside to the outside. Also, the auxiliary member 22 may be a braided tube.

As the constituent material of the auxiliary member 22, a resin material (for example, one or more materials selected from the resin materials cited as the constituent materials of the catheter 12) and a metal material (for example, stainless steel and superelastic alloy) may be cited.

Like the catheter hub 14, for example, the auxiliary member hub 24 is formed from hard resin, and is fixed to a proximal end portion of the auxiliary member 22. The auxiliary member hub 24 includes a hollow circular cylindrical proximal section 70, an engaging projecting section 72 extending from the distal end of the proximal section 70 in the distal end direction, and jutting sections 74 protruding in radially opposite directions from the proximal section 70.

Figure 8:
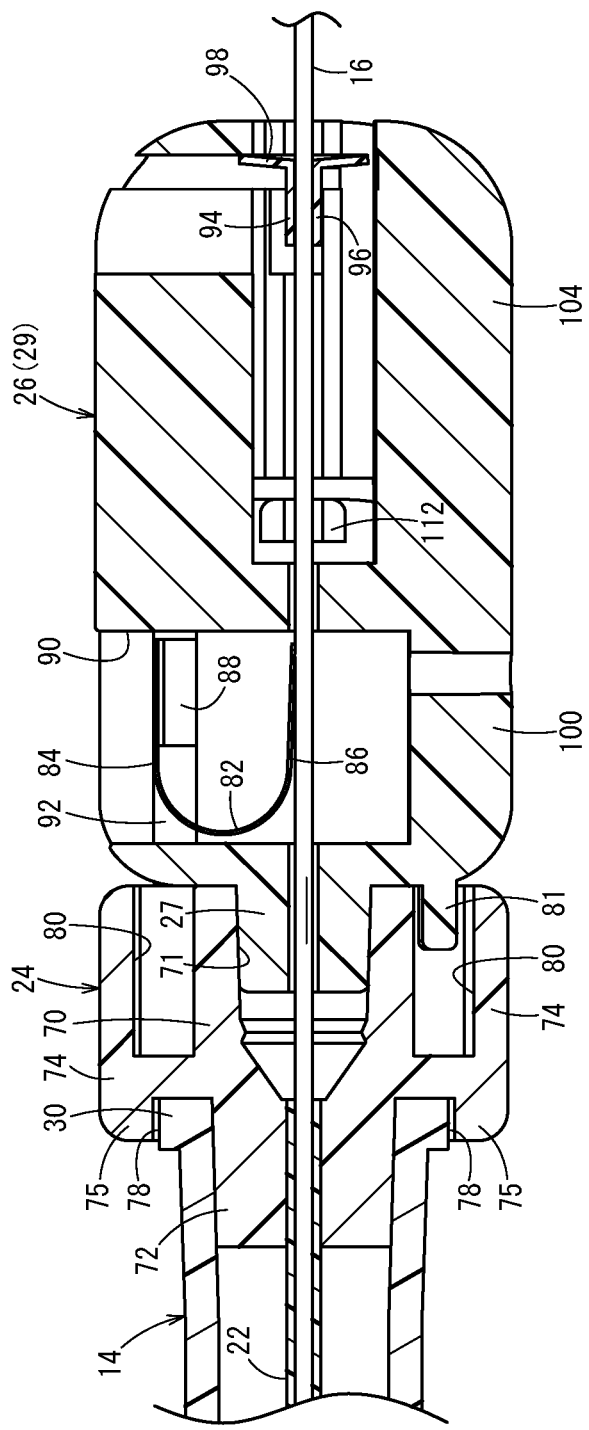
FIG. 8 is a cross-sectional view for describing structures of the auxiliary member hub, the needle protection member, and a shutter (before activation).

As illustrated in FIG. 8, a concave section 71 open in the proximal end direction is formed to the proximal section 70. The inner circumferential surface forming the concave section 71 is formed in a tapered manner with the diameter being reduced toward the distal end direction. In the initial state, a protrusion 27 provided to the needle protection member 26 is taper-engaged to the concave section 71 in a freely detachable manner. Additionally, the mode of coupling of the auxiliary member hub 24 and the needle protection member 26 is not limited to taper engagement, and may be, for example, straight engagement, concave-convex engagement, screw engagement (fastening) or the like.

The outer circumferential surface of the engaging projecting section 72 is formed in a tapered manner with the diameter being reduced toward the distal end direction. In the initial state, the engaging projecting section 72 is taper-engaged to a proximal end inner circumferential portion of the catheter hub 14 in a manner capable of being separated. Additionally, the mode of coupling of the auxiliary member hub 24 and the catheter hub 14 is not limited to taper engagement, and may be straight engagement, concave-convex engagement, screw engagement (fastening) or the like, for example.

Figure 7:
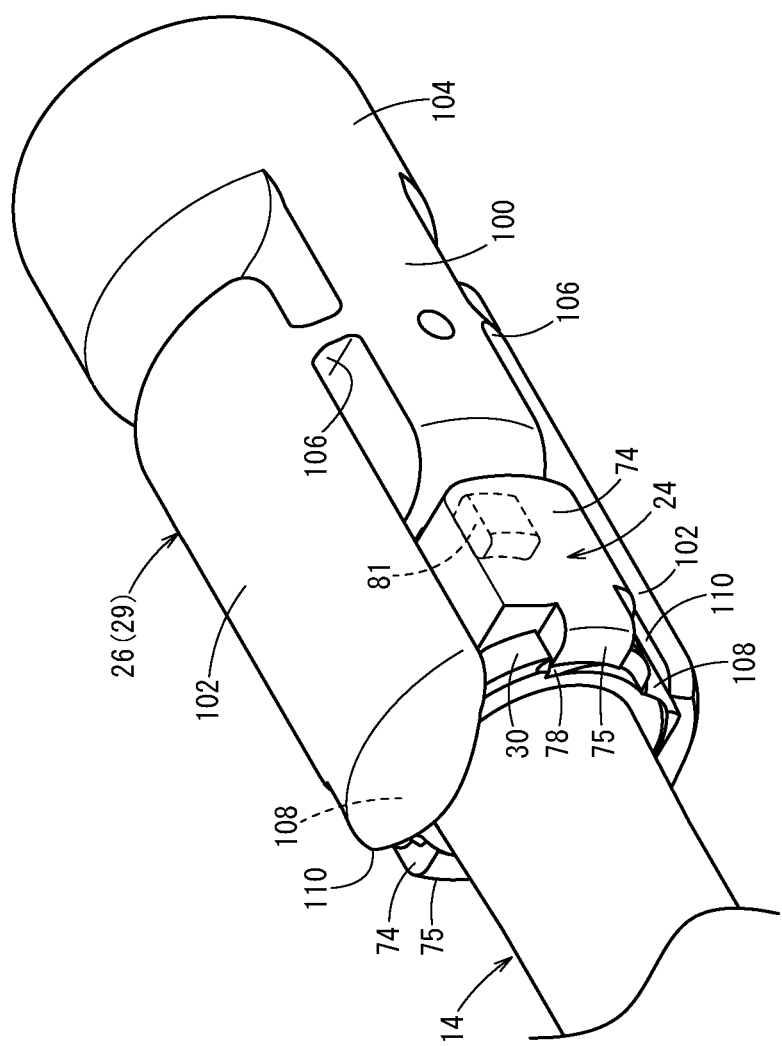
FIG. 7 is a perspective view illustrating a connection state of the catheter hub, an auxiliary member hub, and a needle protection member.
Figure 9:
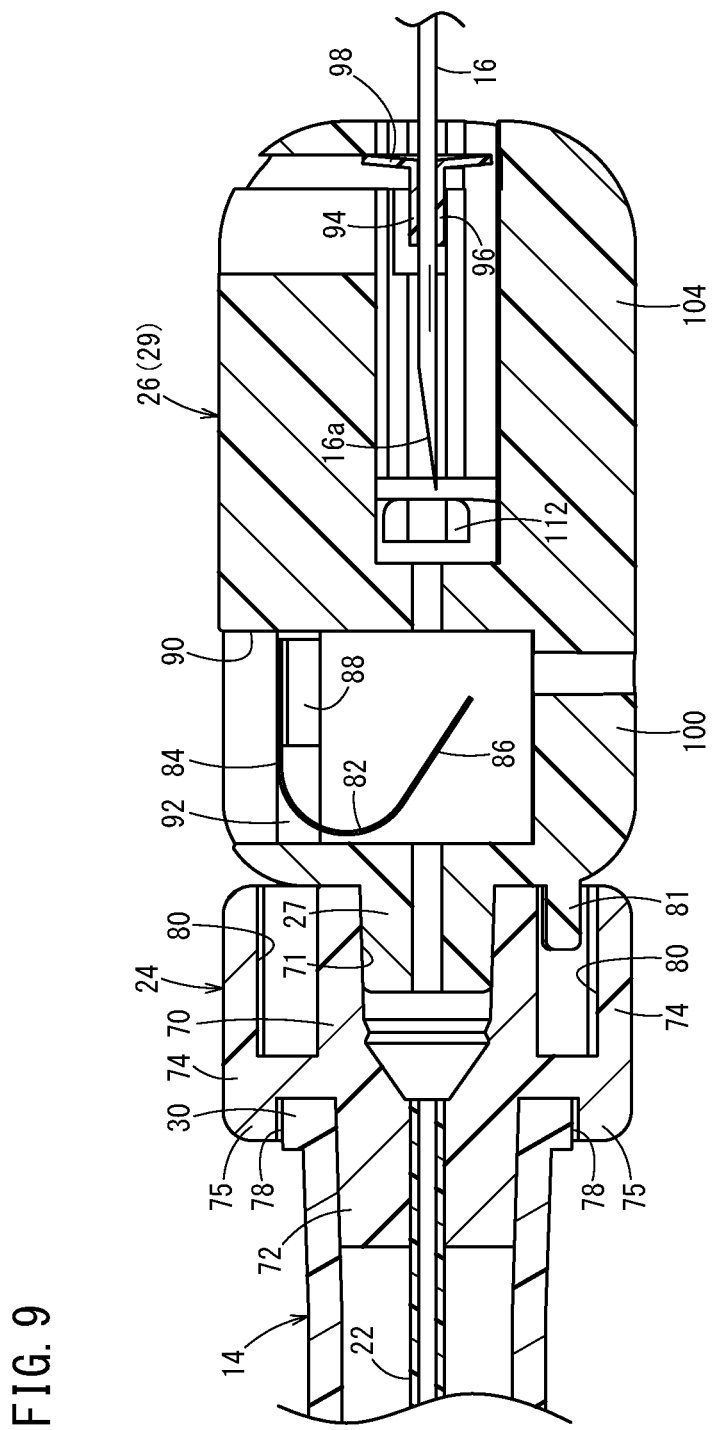
FIG. 9 is a cross-sectional view for describing structures of the auxiliary member hub, the needle protection member, and the shutter (after activation).

As illustrated in FIGS. 7 to 9, an engaging protrusion 75 (a second engagement section) is provided at a distal end of the jutting section 74. In the initial state, the engaging protrusion 75 is inserted in a cut-out engaging concave section 78 (a first engagement section) provided to a proximal end portion (the screw section 30) of the catheter hub 14, and relative rotation of the catheter hub 14 and the auxiliary member hub 24 is thereby obstructed. Also, as illustrated in FIGS. 8 and 9, an engagement hole 80 open in the proximal end direction are provided to the auxiliary member hub 24. In the initial state, a protrusion 81 provided to the needle protection member 26 is inserted in the engagement hole 80 of the auxiliary member hub 24, and relative rotation of the auxiliary member hub 24 and the needle protection member 26 is thereby obstructed.

The catheter hub 14, the auxiliary member hub 24, and the needle protection member 26 are coupled with one another in the manner described above. Thus, in a state where the catheter hub 14 and the auxiliary member hub 24 are coupled and the auxiliary member hub 24 and the needle protection member 26 are coupled, relative rotation of the catheter hub 14 and the needle protection member 26 is obstructed. Accordingly, when a user rotates the needle protection member 26, rotation of the needle protection member 26 is transmitted to the catheter 12 through the auxiliary member hub 24 and the catheter hub 14, and the catheter 12 may be rotated with respect to the inner needle 16. That is, the needle protection member 26 serves also as a rotation operation section 29 which is operated by a user to rotate the catheter 12. It is also possible to provide only one jutting section 74.

The auxiliary member 22 does not have to be provided if the diameter of the catheter 12 of the catheter assembly 10 is relatively large and there is not much need for assistance (support) from the inside to increase the rigidity. In this case, if the auxiliary member hub 24 is provided as it is, the structure of the needle protection member 26 may be the same as the one illustrated, and it is not necessary to use two molds for molding the needle protection member 26 for a case where the auxiliary member 22 is provided and for a case where it is not. That is, in both cases, the needle protection member 26 may be molded by a mold of the same shape.

Furthermore, it is not necessary to provide the auxiliary member hub 24 in the catheter assembly 10. In this case, the proximal end portion of the auxiliary member 22 is directly fixed to the needle protection member 26, and the distal end of the needle protection member 26 is formed to have a shape that engages with the proximal end inner circumferential portion of the catheter hub 14 in a freely detachable manner. Furthermore, the auxiliary member 22 and auxiliary member hub 24 do not necessarily have to be provided to the catheter assembly 10. Also in this case, the distal end of the needle protection member 26 is formed to have a shape which allows engaging with the proximal end inner circumferential portion of the catheter hub 14 in a freely detachable manner.

As illustrated in FIG. 8, a shutter 82 is disposed inside the needle protection member 26. The illustrated shutter 82 is embodied as a flat spring which is formed by bending a metal plate member. The shutter 82 includes a fixed section 84 and a mobile section 86 capable of moving with respect to the fixed section 84. The shutter 82 is further provided with an engaging piece 88 (a barb). In the assembly step, when the shutter 82 is inserted into an arrangement hole 90 provided to the needle protection member 26 in a predetermined direction in a state where the engaging piece 88 is elastically deformed inward, the engaging piece 88 is fitted in a fixing groove 92 provided to the arrangement hole 90, and the shutter 82 is thereby fixed in the arrangement hole 90. Additionally, in the illustrated example, the engaging piece 88 is bent from the fixed section 84 of the shutter 82 toward the mobile section 86, but it may alternatively be bent from the fixed section 84 in the opposite direction from the mobile section 86.

As illustrated in FIG. 8, in the initial state, the shutter 82 is compressed by being pressed by the outer surface of the inner needle 16. When the inner needle 16 moves backward with respect to the needle protection member 26 and the needle tip 16*a* of the inner needle 16 moves toward the proximal end than the shutter 82, as illustrated in FIG. 9, the pressure from the inner needle 16 to the shutter 82 is released, and the shutter 82 is expanded (opened) by elastic restoration force. A needle insertion path inside the needle protection member 26 is thereby blocked.

A retention member 94 is disposed inside a proximal end portion of the needle protection member 26 so that the inner needle 16 does not come out from the needle protection member 26 in the proximal end direction. The retention member 94 includes a tube section 96 through which the inner needle 16 is inserted, and a flange section 98 protruding radially outward from the tube section 96. Although not illustrated in detail, the outer diameter of the inner needle 16 is larger than the inner diameter of the tube section 96 only at the distal end portion, and when the distal end portion with a large diameter moves to the proximal end side of the needle protection member 26, the distal end portion gets caught by the retention member 94 (the tube section 96). The inner needle 16 is thereby prevented from coming out from the proximal end side of the needle protection member 26 where the needle insertion path is blocked by the shutter 82.

As illustrated in FIG. 8, the needle protection member 26 includes a main body section 100 accommodating the shutter 82, and the protrusion 27 protruding from the distal end of the main body section 100 in the distal end direction. Also, as illustrated in FIG. 7, the needle protection member 26 includes a plurality of arms 102 (in the illustrated example, two) that are supported by the main body section 100 in a manner capable of swinging, and a circular cylindrical operator 104 (a finger rest section) provided on the proximal end side of the main body section 100.

The arrangement hole 90 described above is provided to the main body section 100. The operator 104 is a part provided to allow a user to easily perform the rotation operation, described above, by touching the operator 104 with a finger. As illustrated in FIG. 8, the protrusion 81 described above protrudes in the distal end direction from a distal end surface of the main body section 100.

Figure 10:
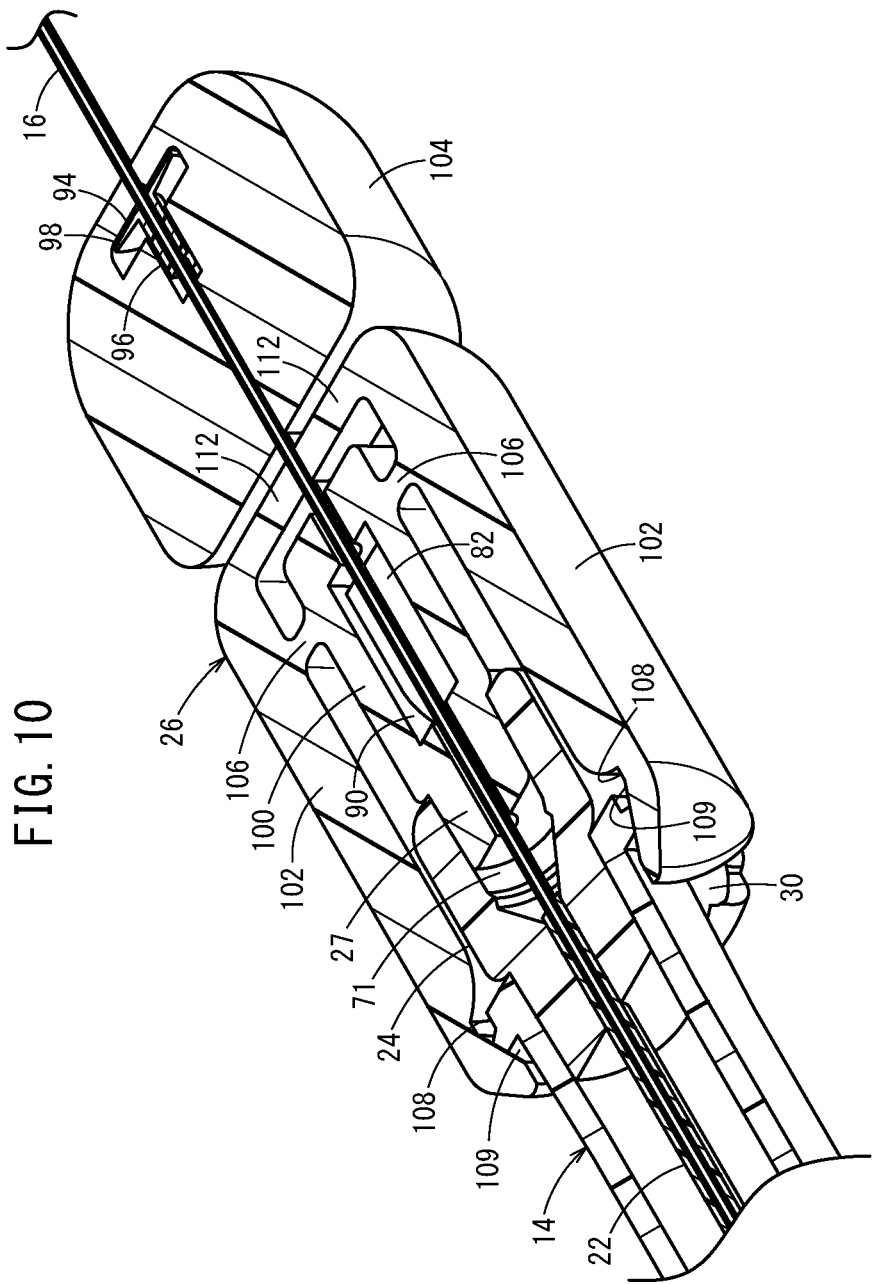
FIG. 10 is a first perspective cross-sectional view illustrating a connection state of the catheter hub, the auxiliary member hub, and the needle protection member.

As illustrated in FIG. 10, the plurality of arms 102 extend approximately parallel to each other, along the inner needle 16. Each arm 102 is connected to the main body section 100 by a connection section 106. The connection section 106 is provided between the distal end and the proximal end of the arm 102, and is thin so as to allow each arm 102 to swing easily.

On the other hand, each arm 102 is made to be relatively thick so that it is not warped easily. An engaging groove 108 is provided on the inside of a distal end portion of each arm 102, and in the initial state, the flange-shaped screw section 30 provided to the catheter hub 14 is placed (fitted) inside the engaging groove 108. The engaging groove 108 has an inclined surface 109 more inclined toward a center line of the needle protection member 26 as it gets closer to the distal end.

On one side in the width direction of the distal end portion of each arm 102, a relatively thick reinforcement section 110 (see FIG. 7) is provided adjacent the engaging groove 108 so that the part where the engaging groove 108 is provided is not warped. The reinforcement section 110 may be provided also on the other side in the width direction of the distal end portion of each arm 102. An inward protrusion 112 protruding inward is provided at a proximal end portion of each arm 102.

The needle protection member 26 is formed from hard resin, for example. The hard resin may be selected from materials cited as examples of the constituent material of the catheter hub 14. The needle protection member 26 is formed such that it can be manufactured in one piece from a resin material.

As illustrated in FIG. 10, in the initial state, inner ends of the inward protrusions 112 are close to or in contact with the outer surface of the inner needle 16. Therefore, inward displacement of the proximal end portions of the arms 102 is obstructed by the inner needle 16, and as a result, spreading of the distal end sides of the arms 102 with the connection sections 106 as fulcrums is obstructed. Accordingly, the engagement between the engaging grooves 108 of the arms 102 and the screw section 30 of the catheter hub 14 is maintained, and the catheter hub 14 does not come off from the needle protection member 26.

Figure 11:
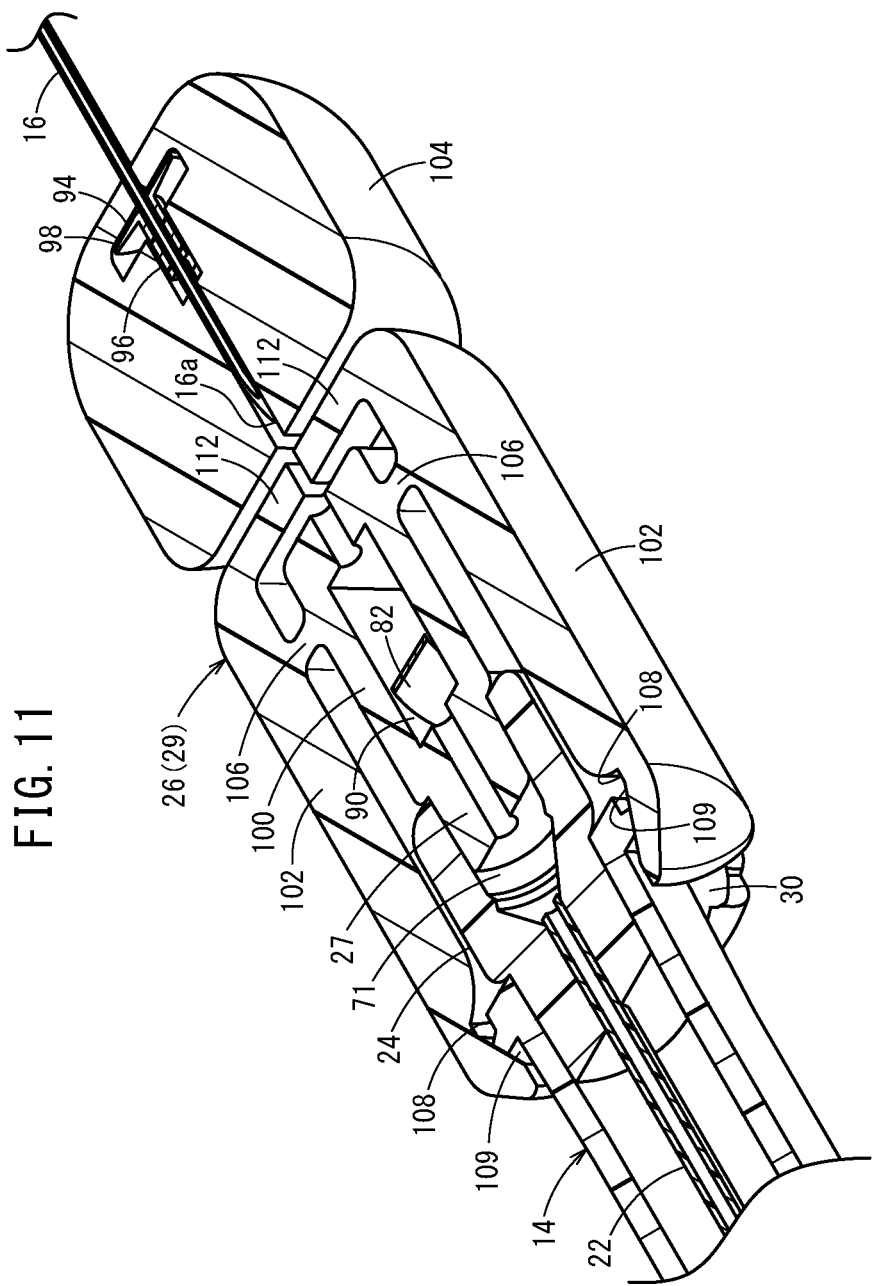
FIG. 11 is a second perspective cross-sectional view illustrating a connection state of the catheter hub, the auxiliary member hub, and the needle protection member.

On the other hand, as illustrated in FIG. 11, when the inner needle 16 moves backward with respect to the needle protection member 26 and the needle tip 16a of the inner needle 16 moves to the proximal end side than the inward protrusions 112 of the arms 102, obstruction by the inner needle 16 of inward displacement of the inward protrusions 112 is released, and the distal end sides of the arms 102 are placed in a state where they are allowed to be spread. Accordingly, when the catheter hub 14 is pulled in the distal end direction with respect to the needle protection member 26, the distal end sides of the arms 102 are opened and the catheter hub 14 is removed.

Next, actions and effects of the catheter assembly 10 configured in the above manner will be described.

According to the catheter assembly 10 in the initial state illustrated in FIG. 1, the catheter hub 14, the auxiliary member hub 24, and the needle protection member 26 are connected together, and the catheter hub 14 is attached to the hub attachment section 48 of the catheter operation member 20, and these are accommodated in the accommodation space 40 of the housing 18 in an integrated manner. Also, in the initial state, the multi-tube section where the catheter 12, the auxiliary member 22, and the inner needle 16 are concentrically overlapped with one another is held by the holding sections 58 (see FIG. 3) of the catheter operation member 20.

As described above, to reduce puncture resistance, the distal end of the catheter 12 is reduced in diameter, and the inner surface of the catheter 12 and the outer surface of the inner needle 16 are in close contact with each other at the reduced diameter part. When this close contact continues for a long time, the inner surface of the catheter 12 and the outer surface of the inner needle 16 may become adhered to each other. This adhesion makes it difficult to perform operation of moving the catheter 12 forward with respect to the inner needle 16 in order to insert the catheter 12 into a blood vessel. Accordingly, the adhesion is released before piercing, by rotating the catheter 12 with respect to the inner needle 16.

Specifically, in the present embodiment, because the needle protection member 26 forms the rotation operation section 29, a user touches the needle protection member 26 exposed from the housing 18 with a finger, and rotates the needle protection member 26 around an axis line in the longitudinal direction of the housing 18. Then, rotation of the needle protection member 26 is transmitted to the catheter 12 through the auxiliary member hub 24 and the catheter hub 14, and the catheter 12 is rotated with respect to the inner needle 16. Adhesion of the inner surface of the catheter 12 and the outer surface of the inner needle 16 may thereby be released.

Additionally, in the case where the catheter hub 14 is exposed from the housing 18 in the initial state, and the catheter hub 14 may be touched at the exposed part, the adhesion may be released by directly touching and rotating the catheter hub 14. Also, in the case where the needle protection member 26 is not provided to the catheter assembly 10, a user may release the adhesion by directly touching and rotating the catheter hub 14 exposed from the housing 18.

Next, a piercing operation of piercing the skin of a patient with the catheter assembly 10 is performed. In the piercing operation, a user (a doctor, a nurse, etc.) grasps the housing 18, presses the distal end portion of the catheter assembly 10

(the distal end portion of the catheter 12 through which the inner needle 16 is inserted) against the patient, and pierces the skin toward a piercing target blood vessel. The inner needle 16 and the distal end portion of the catheter 12 are thereby made to pierce the skin. At the time of piercing, because the catheter 12 is held by the holding sections 58, as described above, even if there is a resistance against piercing, warping of the multi-tube section inside the housing 18 is suppressed. The user is thereby allowed to perform piercing without any uncomfortable feeling.

Figure 12A:
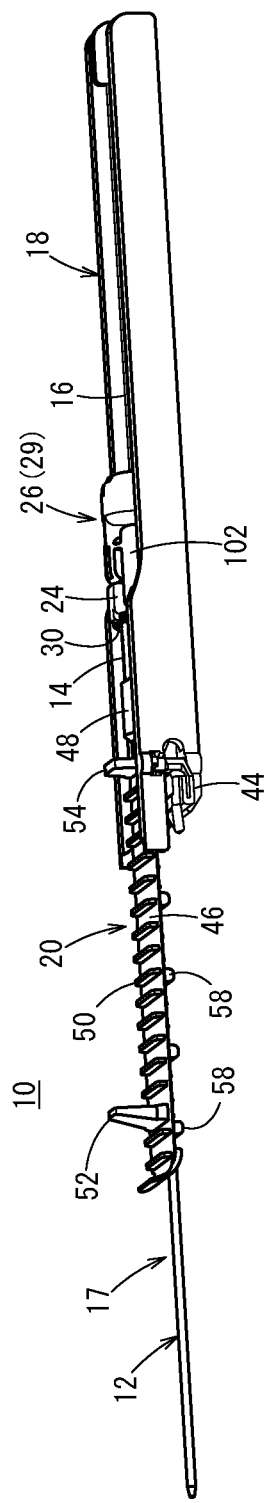
FIG. 12A is a first view describing a method of using the catheter assembly.

Next, as illustrated in FIG. 12A, the user moves the catheter member 17 (the catheter 12 and the catheter hub 14) forward by operating the catheter operation member 20 in the distal end direction while fixing the position of the housing 18. In this case, the user slides the catheter operation member 20 in the distal end direction relative to the housing 18 by pressing a finger against the ribs 50 or the tab 52 of the catheter operation member 20, for example. The catheter 12 is thereby inserted to the target position in the blood vessel.

In FIG. 12A, the catheter operation member 20 is straight, but in reality, the catheter operation member 20 is made to move forward with the operation plate section 46 of the catheter operation member 20 bent upward so that the catheter operation member 20 does not contact the skin of the patient. Bending of the operation plate section 46 is started from the distal end side of the operation plate section 46, and a plurality of holding sections 58 arranged next to one another in the longitudinal direction of the operation plate section 46 come off from the multi-tube section including the catheter 12, one by one from the distal end side toward the proximal end side. Furthermore, during the forward movement, the multi-tube section is supported from below by the support member 44, and thus, downward warping of the multi-tube section is suppressed.

Figure 12B:
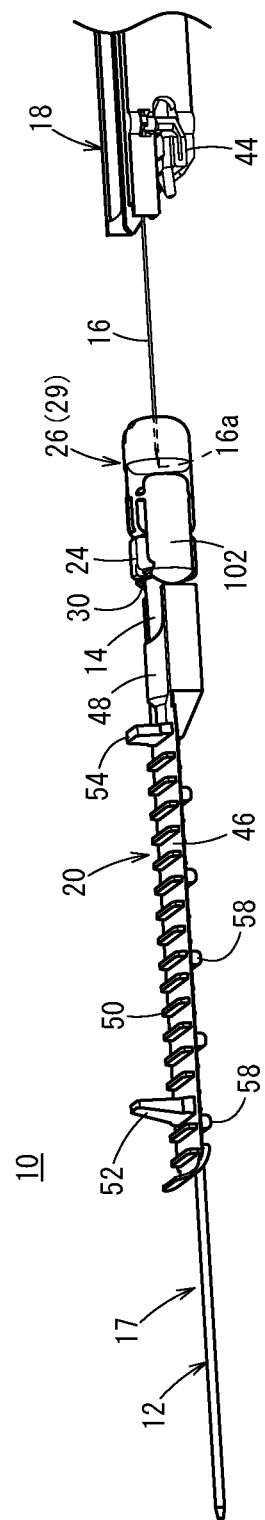
FIG. 12B is a second view describing the method of using the catheter assembly.

Next, the user pulls the housing 18 in the proximal end direction while maintaining the positions of the catheter operation member 20 and the catheter member 17. Accordingly, as illustrated in FIG. 12B, the catheter member 17 and the catheter operation member 20 are completely removed from the housing 18, and also, the inner needle 16 fixed to the housing 18 is removed from the catheter 12.

At this time, a safety function of the needle protection member 26 and the shutter 82 is activated. That is, as illustrated in FIG. 9, when the needle tip 16a moves, inside the needle protection member 26, to the proximal end side than the shutter 82, the shutter 82 blocks the needle insertion path inside the needle protection member 26. This prevents the inner needle 16 from protruding again from the distal end of the needle protection member 26. Also, because the inner needle 16 is prevented by the retention member 94 from coming out from the proximal end side of the needle protection member 26, the needle tip 16a may be kept being desirably protected by the needle protection member 26.

Also, when the needle tip 16a moves, inside the needle protection member 26, to the proximal end side than the inward protrusions 112 of the arms 102, the distal end sides of the arms 102 are placed in a state where they are allowed to be spread. Accordingly, when the housing 18 is further pulled in the proximal end direction from the state in FIG. 12B, coupling between the catheter hub 14 and the needle protection member 26 is released. This causes the needle protection member 26 to be separated from the catheter hub 14, as illustrated in FIG. 13A. Also, at this time, the auxiliary member hub 24 and the needle protection member 26 are coupled together by being engaged, and thus, the auxiliary member hub 24 is pulled by the needle protection member 26 in the proximal end direction, and the auxiliary member 22 is thereby also removed from the catheter 12.

Next, as illustrated in FIG. 13B, the user removes the catheter operation member 20 from the catheter hub 14. The catheter member 17 is thereby made to remain on the patient. Additionally, depending on the preference of the user, the catheter operation member 20 may be kept mounted on the catheter hub 14.

Next, a connector of a transfusion tube, not illustrated, is connected to the proximal end side of the catheter member 17 (the proximal end portion of the catheter hub 14) from which the inner needle 16 and the auxiliary member 22 have been pulled out, and administration of a transfusion to the patient from the transfusion tube is performed.

Additionally, in the description given above, at the time of separating the needle protection member 26 from the catheter hub 14, the auxiliary member hub 24 is kept being connected to the needle protection member 26, and the auxiliary member 22 is removed from the catheter 12. However, depending on the preference of the user, the needle protection member 26 and the auxiliary member hub 24 may also be separated from each other at the time of separation of the needle protection member 26 from the catheter hub 14, and an assembly of the auxiliary member 22 and the catheter 12 may be inserted into the blood vessel.

As described above, according to the catheter assembly 10, the catheter hub 14 accommodated in the housing 18 is, in the initial state, allowed to rotate with respect to the inner needle 16 and the housing 18. Accordingly, by rotating the catheter hub 14 supporting the catheter 12 before using the catheter assembly 10, adhesion of the inner surface of the catheter 12 and the outer surface of the inner needle 16 may be released.

When using the catheter assembly 10, the distal end of the catheter 12 may get caught on a blood vessel wall during insertion of the catheter 12 into the blood vessel, thereby making insertion difficult. In this case, according to a conventional catheter assembly where the catheter hub is connected to the distal end of the needle hub, a procedure of inserting the catheter into a blood vessel while rotating the same is sometimes taken. However, because the catheter assembly of JP 2013-529111 A does not allow rotation of the catheter, the procedure of inserting the catheter into a blood vessel while rotating the same cannot be taken when the distal end of the catheter gets caught on a blood vessel wall.

On the other hand, with the catheter assembly 10, the catheter hub 14 may be rotated with respect to the inner needle 16 and the housing 18 in all the range from a first position corresponding to the initial state (FIG. 1) to a second position (FIG. 12A) where the catheter hub 14 has been moved forward by a predetermined distance with respect to the housing 18 so as to insert the catheter 12 into a blood vessel by a predetermined length. According to this structure, when the distal end of the catheter 12 gets caught on the blood vessel wall during insertion of the catheter 12 into the blood vessel, the catheter 12 may be inserted into the blood vessel while being rotated.

The catheter assembly 10 includes the rotation operation section 29, which is coupled to the catheter hub 14 in a manner not capable of relative rotation, and the rotation operation section 29 is exposed from the housing 18 in a state where the catheter hub 14 is accommodated in the housing 18. According to this structure, it is possible to touch and rotate the rotation operation section 29 exposed from the housing 18 by hand, and adhesion may be easily released.

According to the catheter assembly 10, the rotation operation section 29 may be detached from the catheter hub 14, and thus the part remaining on the skin of a patient may be made small.

According to the catheter assembly 10, the catheter hub 14 and the rotation operation section 29 are coupled through the auxiliary member hub 24 without being capable of relative rotation. According to this structure, rotation of the rotation operation section 29 is transmitted to the catheter 12 through the auxiliary member hub 24 and the catheter hub 14, and the catheter 12 may be rotated.

According to the catheter assembly 10, the catheter hub 14 is capable of rotating with respect to the catheter operation member 20 and the catheter 12, and thus, also in the case where the catheter operation member 20 is provided, rotation of the catheter hub 14 is not prevented by the catheter operation member 20. Accordingly, adhesion of the catheter 12 and the inner needle 16 may be reliably released.

According to the catheter assembly 10, the rotation operation section 29 forms the needle protection member 26 which covers at least the distal end of the inner needle 16 when the inner needle 16 is removed from the catheter 12. According to this structure, because the rotation operation section 29 functions also as the needle protection member 26, the rotation operation section 29 and the needle protection member 26 do not have to be separately provided, and an increase in the number of components or complication of the structure caused by having to provide the rotation operation section 29 may be suppressed.

Also, according to the catheter assembly 10, the needle protection member 26 is provided at the proximal end portion of the auxiliary member hub 24, and thus, erroneous piercing after removal of the inner needle 16 from the catheter 12 may be effectively prevented.

Furthermore, according to the catheter assembly 10, when the inner needle 16 is removed from the catheter 12, the auxiliary member hub 24 is allowed to be detached from the catheter hub 14. According to this structure, when the housing 18 (needle hub) is moved backward to remove the inner needle 16 from the catheter 12, lock (fixation) between the catheter hub 14 and the auxiliary member hub 24 is automatically released. Accordingly, a user may easily separate the auxiliary member hub 24 from the catheter hub 14 without having to separately perform an operation of releasing the lock between the catheter hub 14 and the auxiliary member hub 24, and burden regarding operation is small.

Particularly, according to the catheter assembly 10, the needle protection member 26 is engaged with the catheter hub 14 disposed on the distal end side of the auxiliary member hub 24 in a manner capable of being released, and the auxiliary member hub 24 is held between the needle protection member 26 and the catheter hub 14 in a state where the needle protection member 26 is engaged with the catheter hub 14. According to this structure, when engagement of the needle protection member 26 and the catheter hub 14 is released, the auxiliary member hub 24 is allowed to be separated from the catheter hub 14. Accordingly, the auxiliary member 22 may be easily removed from the catheter 12.

Moreover, according to the catheter assembly 10, the needle protection member 26 is structured to release the catheter hub 14 after the distal end of the inner needle 16 is accommodated inside the needle protection member 26. According to this structure, erroneous piercing may be reliably prevented because the distal end (the needle tip 16a) of the inner needle 16 is invariably covered by the needle protection member 26 when the needle protection member 26 is separated from the catheter hub 14.

Furthermore, according to the catheter assembly 10, the auxiliary member hub 24 is coupled to the needle protection member 26 in a manner capable of separating therefrom, and thus, depending on the preference of a user, an assembly of the auxiliary member 22 and the catheter 12 may be inserted into a blood vessel with the auxiliary member hub 24 separated from the needle protection member 26.

Moreover, according to the catheter assembly 10, after the distal end of the inner needle 16 is accommodated inside the needle protection member 26, the auxiliary member hub 24 may be separated from the needle protection member 26. According to this structure, erroneous piercing may be reliably prevented because the distal end of the inner needle 16 is invariably covered by the needle protection member 26 when the auxiliary member hub 24 is separated from the needle protection member 26.

Additionally, to facilitate insertion of the catheter 12 into a blood vessel, the catheter assembly 10 may be provided with a guide wire which is to be slidably inserted through the lumen of the inner needle 16 in an axial direction and which may protrude from the distal end of the inner needle 16. In the case where such a guide wire is provided, after the distal end portion of the catheter assembly 10 pierces the skin of a patient, the guide wire is made to protrude from the distal end of the inner needle 16 and to be inserted into the blood vessel by a predetermined length. Then, the catheter 12 is moved into the blood vessel along the guide wire.

The present invention is not limited to the embodiment described above, and various alterations are possible without departing from the spirit of the present invention.

What is claimed is:

1. A catheter assembly comprising:
    a catheter;
    a catheter hub fixed to a proximal end portion of the catheter;
    an inner needle disposed inside the catheter;
    a housing supporting the inner needle; and
    a catheter operation member connected to the catheter hub and being displaceable with respect to the housing along a longitudinal direction of the housing,
    wherein, when the catheter assembly is in an initial state in which a distal end of the inner needle protrudes from a distal end of the catheter, an entirety of the catheter hub and a portion of the catheter are accommodated inside a space defined by the housing, and
    wherein the catheter hub is configured to rotate with respect to the inner needle and the housing when the catheter hub is accommodated inside the space defined by the housing, and
    wherein the catheter hub is configured to rotate with respect to the catheter operation member.

2. The catheter assembly according to claim 1, wherein the catheter hub is configured to rotate with respect to the inner needle and the housing over an entire range from a first position corresponding to the initial state to a second position after forward movement of the catheter hub by a predetermined distance with respect to the housing.

3. The catheter assembly according to claim 1, further comprising:
    a rotation operation section coupled to the catheter hub such that the rotation operation section is not capable of relative rotation with respect to the catheter hub,
    wherein the rotation operation section is exposed from the housing when the catheter hub is accommodated inside the space defined by the housing.

4. The catheter assembly according to claim 3, wherein the rotation operation section is detachable from the catheter hub.

5. The catheter assembly according to claim 3, further comprising:
an auxiliary member disposed between the catheter and the inner needle, and extending along the catheter; and
an auxiliary member hub fixed to a proximal end portion of the auxiliary member,
wherein the catheter hub and the rotation operation section are coupled via the auxiliary member hub such that the catheter hub and the rotation operation section are not capable of relative rotation with respect to the auxiliary member hub.

6. The catheter assembly according to claim 3, wherein the rotation operation section forms a needle protection member configured to cover at least a distal end of the inner needle when the inner needle is removed from the catheter.

7. The catheter assembly according to claim 3, wherein the housing includes an opening portion configured to expose the rotation operation section.

8. A catheter assembly comprising:
a catheter;
a catheter hub fixed to a proximal end portion of the catheter;
an inner needle disposed inside the catheter;
a housing supporting the inner needle, the housing accommodating the catheter hub when the catheter assembly is in an initial state in which a distal end of the inner needle is protruding from a distal end of the catheter; and
a rotation operation section coupled to the catheter hub such that the rotation operation section is not capable of relative rotation with respect to the catheter hub,
wherein the rotation operation section is exposed from the housing when the housing is in a state in which the catheter hub is accommodated inside the housing,
wherein the rotation operation section is detachable from the catheter hub, and
wherein the catheter hub is configured to rotate with respect to the inner needle and the housing when the catheter hub is accommodated inside the housing.

9. The catheter assembly according to claim 8, wherein, when the catheter assembly is in the initial state, the catheter hub is configured to rotate with respect to the inner needle and the housing.

10. The catheter assembly according to claim 8, wherein the catheter hub is configured to rotate with respect to the inner needle and the housing over an entire range from a first position corresponding to the initial state to a second position after forward movement of the catheter hub by a predetermined distance with respect to the housing.

11. The catheter assembly according to claim 8, further comprising:
an auxiliary member disposed between the catheter and the inner needle, and extending along the catheter; and
an auxiliary member hub fixed to a proximal end portion of the auxiliary member,
wherein the catheter hub and the rotation operation section are coupled via the auxiliary member hub such that the catheter hub and the rotation operation section are not capable of relative rotation with respect to the auxiliary member hub.

12. The catheter assembly according to claim 8, further comprising:
a catheter operation member connected to the catheter hub and being displaceable with respect to the housing along a longitudinal direction of the housing,
wherein the catheter hub is configured to rotate with respect to the catheter operation member.

13. The catheter assembly according to claim 8, wherein the rotation operation section forms a needle protection member configured to cover at least a distal end of the inner needle when the inner needle is removed from the catheter.

14. The catheter assembly according to claim 8, wherein the housing includes an opening portion configured to expose the rotation operation section.

15. A catheter assembly comprising:
a catheter;
a catheter hub fixed to a proximal end portion of the catheter;
an inner needle disposed inside the catheter;
a housing supporting the inner needle, the housing accommodating the catheter hub when the catheter assembly is in an initial state in which a distal end of the inner needle is protruding from a distal end of the catheter;
a rotation operation section coupled to the catheter hub such that the rotation operation section is not capable of relative rotation with respect to the catheter hub;
an auxiliary member disposed between the catheter and the inner needle, and extending along the catheter; and
an auxiliary member hub fixed to a proximal end portion of the auxiliary member,
wherein the rotation operation section is exposed from the housing when the housing is in a state in which the catheter hub is accommodated inside the housing,
wherein the catheter hub and the rotation operation section are coupled via the auxiliary member hub such that the catheter hub and the rotation operation section are not capable of relative rotation with respect to the auxiliary member hub, and
wherein the catheter hub is configured to rotate with respect to the inner needle and the housing when the catheter hub is accommodated inside the housing.

16. The catheter assembly according to claim 15, wherein, when the catheter assembly is in the initial state, the catheter hub is configured to rotate with respect to the inner needle and the housing.

17. The catheter assembly according to claim 15, wherein the catheter hub is configured to rotate with respect to the inner needle and the housing over an entire range from a first position corresponding to the initial state to a second position after forward movement of the catheter hub by a predetermined distance with respect to the housing.

18. The catheter assembly according to claim 15, further comprising:
a catheter operation member connected to the catheter hub and being displaceable with respect to the housing along a longitudinal direction of the housing,
wherein the catheter hub is configured to rotate with respect to the catheter operation member.

19. The catheter assembly according to claim 15, wherein the rotation operation section forms a needle protection member configured to cover at least a distal end of the inner needle when the inner needle is removed from the catheter.

20. The catheter assembly according to claim 15, wherein the housing includes an opening portion configured to expose the rotation operation section.

* * * * *